(12) United States Patent
Reinke et al.

(10) Patent No.: US 9,002,470 B2
(45) Date of Patent: Apr. 7, 2015

(54) SUPPLY NOISE REJECTION IN IMPLANTABLE MEDICAL DEVICES

(71) Applicant: Medtronic, Inc., Minneapolis, MN (US)

(72) Inventors: James D. Reinke, Maple Grove, MN (US); Charles R. Gordon, Phoenix, AZ (US); Kevin P. Kuehn, Shoreview, MN (US); Michael B. Terry, Camas, WA (US)

(73) Assignee: Medtronic, Inc., Minneapolis, MN (US)

( * ) Notice: Subject to any disclaimer, the term of this patent is extended or adjusted under 35 U.S.C. 154(b) by 31 days.

(21) Appl. No.: 14/060,649

(22) Filed: Oct. 23, 2013

(65) Prior Publication Data

US 2015/0073507 A1 Mar. 12, 2015

Related U.S. Application Data

(60) Provisional application No. 61/876,454, filed on Sep. 11, 2013.

(51) Int. Cl.
*A61N 1/00* (2006.01)
*A61N 1/378* (2006.01)

(52) U.S. Cl.
CPC .................................... *A61N 1/3787* (2013.01)

(58) Field of Classification Search
USPC .......................................................... 607/61
See application file for complete search history.

(56) References Cited

U.S. PATENT DOCUMENTS

| | | | |
|---|---|---|---|
| 3,153,180 A | 10/1964 | Bellmore | |
| 3,943,936 A | 3/1976 | Rasor et al. | |
| 4,374,382 A | 2/1983 | Markowitz | |
| 4,376,811 A | 3/1983 | Goebel | |
| 4,556,063 A | 12/1985 | Thompson et al. | |
| 5,127,404 A | 7/1992 | Wyborny et al. | |
| 5,306,581 A | 4/1994 | Taylor et al. | |
| 5,700,299 A | 12/1997 | Clark | |
| 5,749,910 A | 5/1998 | Brumwell et al. | |
| 5,776,632 A | 7/1998 | Honegger | |

(Continued)

FOREIGN PATENT DOCUMENTS

WO  WO 2013/067496 A2  5/2013

OTHER PUBLICATIONS (PCT/US2014/053875) PCT Notification of Transmittal of the International Search Report and the Written Opinion of the International Searching Authority.

(Continued)

*Primary Examiner* — Robert N Wieland
(74) *Attorney, Agent, or Firm* — Evans M. Mburu; Stephen W. Bauer

(57) ABSTRACT

The present invention provides an implantable medical device having at least two electrodes coupled to the device housing. The electrodes may be configured for sensing physiological signals such as cardiac signals and alternatively for providing an electrical stimulation therapy such as a pacing or defibrillation therapy. In accordance with aspects of the disclosure, the device housing provides a hermetic enclosure that includes a first housing section that is hermetically coupled to a second housing section. At least one of the at least two electrodes is coupled to an exterior surface of the first housing section that encloses the battery components of the device. The first housing section is electrically insulated from the cathode and anode of the battery.

16 Claims, 5 Drawing Sheets

(56) References Cited

U.S. PATENT DOCUMENTS

| | | |
|---|---|---|
| 5,905,001 A | 5/1999 | Elliott et al. |
| 5,987,352 A | 11/1999 | Klein et al. |
| 6,238,813 B1 | 5/2001 | Maile et al. |
| 6,451,483 B1 | 9/2002 | Probst et al. |
| 6,586,134 B2 | 7/2003 | Skoumpris |
| 6,622,046 B2 | 9/2003 | Fraley et al. |
| 6,946,220 B2 | 9/2005 | Probst et al. |
| 7,070,881 B2 | 7/2006 | Kishiyama et al. |
| 7,292,890 B2 | 11/2007 | Whitehurst et al. |
| 7,442,465 B2 | 10/2008 | Kim et al. |
| 7,640,061 B2 * | 12/2009 | He et al. .......................... 607/36 |
| 8,032,227 B2 | 10/2011 | Parramon et al. |
| 8,359,098 B2 | 1/2013 | Lund et al. |
| 2003/0134185 A1 | 7/2003 | Nakahara et al. |
| 2005/0021108 A1 | 1/2005 | Klosterman et al. |
| 2005/0042561 A1 | 2/2005 | Hu et al. |
| 2006/0123622 A1 | 6/2006 | Guy |
| 2006/0222942 A1 | 10/2006 | Zhao et al. |
| 2007/0150020 A1 | 6/2007 | Hokanson et al. |
| 2007/0179552 A1 | 8/2007 | Dennis et al. |
| 2007/0180686 A1 | 8/2007 | Woo |
| 2010/0305653 A1 | 12/2010 | Lund et al. |
| 2011/0247204 A1 | 10/2011 | Viavattine |

OTHER PUBLICATIONS

Gordon, et al., "Implantable Medical Devices with Power Supply Noise Isolation", U.S. Appl. No. 14/060,646, filed Oct. 23, 2013, 20 pages.

* cited by examiner

SUPPLY NOISE REJECTION IN IMPLANTABLE MEDICAL DEVICES

CROSS-REFERENCE TO RELATED APPLICATION

This application claims the benefit of priority from U.S. Provisional Application No. 61/876,454, filed Sep. 11, 2013, which is incorporated herein by reference in its entirety.

FIELD

The disclosure relates generally to implantable medical devices of the type comprising integrated circuitry for performing monitoring of a physiologic state and/or therapy delivery. In particular, the disclosure pertains to an implantable device having an exposed energy source case.

BACKGROUND

Implantable medical devices are used to monitor and treat a variety of conditions. Examples of implantable medical devices are implantable loop recorders, implantable pacemakers and implantable cardioverter-defibrillators (ICDs), which are electronic medical devices that monitor the electrical activity of the heart and/or provide electrical stimulation to one or more of the heart chambers, when necessary. For example, cardiac signals may be monitored by an implantable device to detect an arrhythmia, i.e., a disturbance in heart rhythm, with appropriate electrical stimulation pulses being provided, at a controlled rate, to selected chambers of the heart in order to correct the arrhythmia and restore the proper heart rhythm.

The implantable medical devices are preferably designed with shapes that are easily tolerated in the patient's body while minimizing patient discomfort. As a result, the corners and edges of the devices are typically designed with generous radii to present a package having smoothly contoured surfaces. It is also desirable to minimize the volume occupied by the devices as well as their mass to further limit patient discomfort. As a result, the devices continue to become thinner, smaller, and lighter.

In order to perform their monitoring, pacing and/or cardioverting-defibrillating functions, the devices must have an energy source, e.g., at least one battery. The batteries employ packaging techniques that enclose the internal components in a casing which is further enclosed in a housing of the implantable medical device. While these battery packages have proven effective for housing and electrically insulating the battery components, there are various inefficiencies associated with the batteries.

One challenge is the excess volumetric size of the implantable medical device caused by placing these batteries within the contoured implantable medical device. As stated above, implantable medical devices are preferably designed with corners and edges having generous radii to present a package having smoothly contoured surfaces. When the battery is placed within the contoured implantable device, the contours of these devices do not necessarily correspond and thus the volume occupied within the implantable device cannot be optimally minimized to further effectuate patient comfort.

Another challenge associated with the conventional battery construction pertains to the electrical connections from the batteries to various components of the implantable device. In a typical implantable device battery, the battery enclosures are formed from metallic or other conductive material. Thus, interconnection inefficiency arises due to the manufacturing limitations and material properties of the battery that impact the device performance.

In accordance with techniques of conventional battery construction such as that disclosed in U.S. Pat. No. 7,442,465, a passive connection of one of the anode or cathode (battery electrodes) is made to the case so that the battery case itself functions as a negative or positive terminal. Such conventional construction requiring that the battery case be connected to one of the two battery terminals in the device poses a challenge to the miniaturization of the implantable medical devices.

For the foregoing reasons, there is a need for an improved implantable medical device assembly with efficient utilization of the device housing.

SUMMARY OF THE INVENTION

The present invention provides solutions to one or more challenges existing in the prior art respecting efficient designs for enclosures of energy sources of implantable medical devices. Among the challenges in the prior art is the lack of an enclosure for an energy source that is designed for use with sensing and or pacing electrodes.

An implantable medical device is disclosed that is implantable in a biological tissue. The device includes an energy storage device (such as a battery) having internal components and a battery case (enclosure) that encloses the internal components. The battery case forms a portion of the housing for the implantable medical device and has an outer surface that is exposed to biological material and fluids of a patient.

The outer surface of the battery case is coupled to at least one electrode that is configured for sensing and/or providing electrical stimulation to the patient. The battery components are electrically isolated from the battery case to isolate the physiological signals sensed by the sensing electrodes from the current flowing through the battery.

In one embodiment, the battery case is coupled to a circuit case that houses operational circuit for controlling the functions of the implantable medical device. Together, the battery case and the circuit case are coupled to form the housing of the implantable medical device.

A feedthrough assembly is provided to separate the internal chamber of the battery case from the internal chamber of the circuit case. A current pathway is defined at the feedthrough assembly to conductively couple the battery components to the operational circuit. The current pathway includes a supply pathway from the battery to the operational circuit and a return pathway from the operational circuit back to the battery.

Still further, an implantable medical device is disclosed that is implantable in a biological tissue. The device includes a battery with an anode, a cathode, and a battery case that encloses the anode and the cathode. The battery case has an inner surface and an outer surface, and the anode and the cathode are disposed within a cavity defined by the inner surface and are electrically isolated from the battery case. The battery also includes a first electrode that is electrically connected to the outer surface of the battery case. The outer surface of the battery case is exposed to the biological tissue. The electrical isolation of the battery case from the active battery components is configured to limit or eliminate artifacts (noise signals) on a signal sensed by the first electrode.

Additionally, a method of constructing an implantable medical device is disclosed. The method tasks include providing a hermetically sealed housing having a battery case and a circuit case, forming a first electrode on an exterior surface of the battery case, coupling a second electrode on the housing, coupling at least first and second feedthroughs to the battery case, wherein the first and second feedthroughs include a positive terminal and a negative terminal of the battery, connecting an operational circuit to the positive and negative terminals, forming a third terminal on the battery case that is directly coupled to the operational circuit and decoupled from the current pathway, connecting the first electrode to the operational circuit through the signal pathway, connecting the second electrode to the operational circuit, enclosing the operational circuit within the circuit case, and coupling the battery case to the circuit case.

These and other features and advantages of the present invention will be set forth or will become more fully apparent in the description that follows and in the appended claims. The features and advantages may be realized and obtained by means of the instruments and combinations particularly pointed out in the appended claims. Furthermore, the features and advantages of the invention may be learned by the practice of the invention or will be apparent from the description, as set forth hereinafter.

BRIEF DESCRIPTION OF THE FIGURES

Various exemplary embodiments of the compositions and methods according to the invention will be described in detail, with reference to the following figures wherein.

DETAILED DESCRIPTION OF THE EXEMPLARY EMBODIMENTS

The invention and the various features and advantageous details thereof are explained more fully with reference to the non-limiting embodiments that are illustrated in the accompanying drawings and detailed in the following description. Descriptions of well-known components and processing techniques are omitted so as not to unnecessarily obscure the invention in detail but such descriptions are, nonetheless, included in the disclosure by incorporation by reference of the citations discussed. It should be understood, however, that the detailed description and the specific examples, while indicating preferred embodiments of the invention, are given by way of illustration only and not by way of limitation. Various substitutions, modifications, additions and/or rearrangements within the spirit and/or scope of the underlying inventive concept will become apparent to those skilled in the art from this detailed description.

The present disclosure facilitates the use of a battery case (enclosure) of an implantable medical device (IMD) as an electrode for sensing physiological signals. Exemplary IMDs may include implantable loop recorders (e.g., Medtronic's Reveal™ implantable loop recorder) or implantable pacemakers and implantable cardioverter-defibrillators (such as a leadless pacemaker or cardioverter-defibrillator). In using the battery case as an electrode, supply currents associated with delivering of energy from the battery generate artifacts (noise signals) that corrupt the physiological signal. If uncontrolled, the noise signal causes over-detection leading to false sensed events or under-detection leading to missed sensed events.

Figure 1:
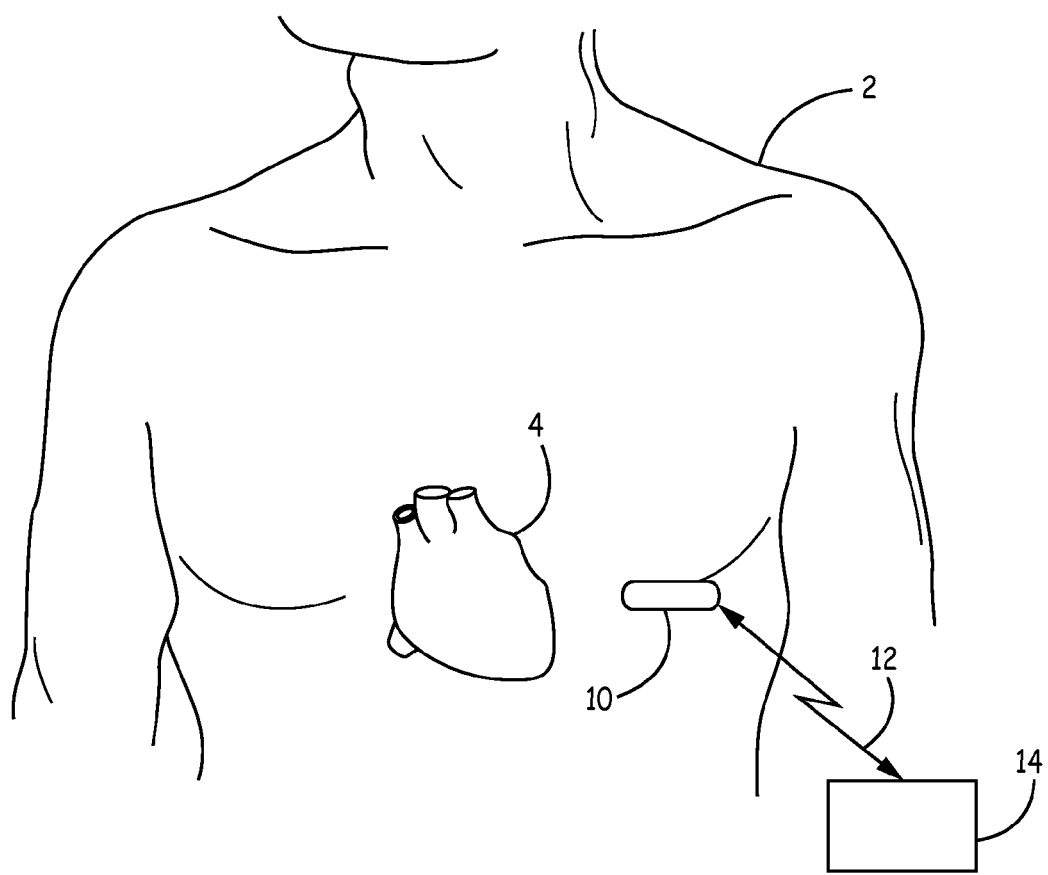
FIG. 1 is a functional schematic diagram of an implantable medical system implanted in a patient according to a preferred embodiment of the present invention.

FIG. 1 is a functional schematic diagram of an IMD according to a preferred embodiment of the present invention. This diagram illustrating a cardiac implementation of the IMD should be taken as exemplary of the type of device in which the invention may be embodied, and not as limiting, as it is believed that the invention may usefully be practiced in a wide variety of device implementations, including devices for monitoring and/or providing therapies such as stimulation of cardiac, nerve or other tissue.

In FIG. 1, a frontal view of a patient 2 in whom an IMD 10 may be implanted subcutaneously is shown with a typical implant location referenced thereon (other implant locations may be utilized). In an alternative implementation, IMD 10 may be configured for implantation within a chamber of heart 4, or on an exterior wall of heart 4, or within a blood vessel. The IMD 10 senses cardiac electrical activation signals via electrodes (not shown in FIG. 1) from heart 4. A communication link 12 allows 2-way telemetry communication between IMD 10 and an external device (typically a programmer) 14. Programmer 14 and communication link 12 suitable for use in the practice of the present invention are known. Known programmers typically communicate with an implanted device such as IMD 10 via a bi-directional radio-frequency telemetry link, so that the programmer 14 can transmit control commands and operational parameter values to be received by the IMD 10, and so that the IMD 10 can communicate captured and stored diagnostic and operational data to the programmer 14. Programmers 14 believed to be suitable for the purposes of practicing the present invention include the Models 9790 and CareLink® programmers, commercially available from Medtronic, Inc., Minneapolis, Minn. Various telemetry systems for providing the necessary communications channels between programmer 14 and an IMD 10 have been developed and are well known in the art and are discussed, for example, in the following U.S. patents: U.S. Pat. No. 5,127,404 to Wyborny et al. entitled "Telemetry Format for Implanted Medical Device"; U.S. Pat. No. 4,374,382 to Markowitz entitled "Marker Channel Telemetry System for a Medical Device"; and U.S. Pat. No. 4,556,063 to Thompson et al. entitled "Telemetry System for a Medical Device".

Figure 2:
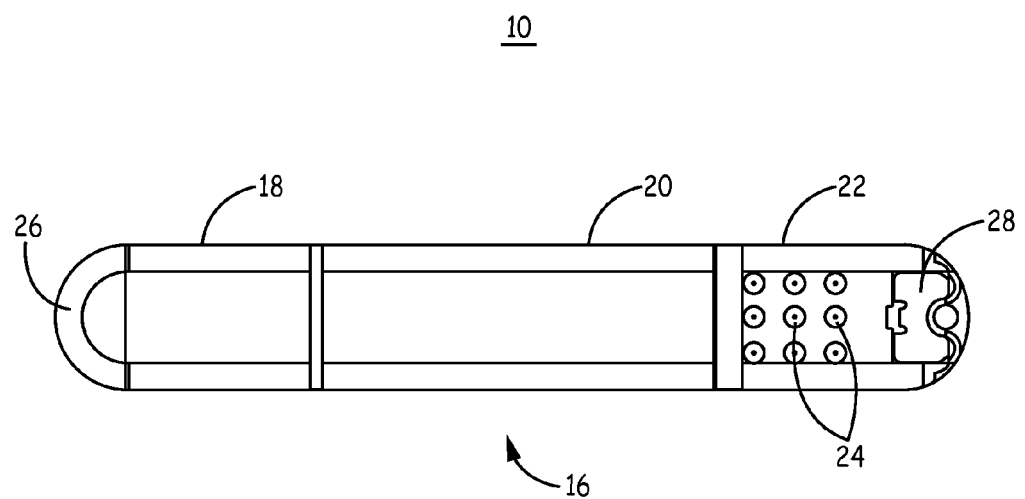
FIG. 2 depicts a perspective view of an exemplary implantable medical device.

FIG. 2 depicts a perspective view of an exemplary IMD 10. IMD 10 includes a housing 16 that encloses an energy source, such as a battery (not shown), and operational circuitry (not shown). The housing 16 may include a battery case 18 enclosing the battery, a circuit case 20 enclosing the operational circuitry and a cap 22. The battery case 18, circuit case 20 and cap 22 may be integrally formed as a single unitary piece or formed from discrete components that are separately formed and coupled in an end-to-end configuration to form a hermetically sealed housing 16.

Battery case 18, circuit case 20, and cap 22 may each be constructed from stainless steel, titanium, or other biocompatible materials. Alternatively, cap 22 may be made out of an insulated material such as plastic or ceramic and may include fixation components 24.

The battery case 18 can be hollow and cylindrical with an inner surface that defines a cavity for enclosing the internal active battery components. The outer surface can be circular, elliptical, ovate, or any other suitable shape. It will be appreciated that the battery case 18 can be the outermost surface of the battery assembly so that the case 18 forms a portion of the housing 16 and the patient 2 is directly exposed to (in direct contact with) the battery case 18.

A sense/pace electrode 26 may be disposed on the battery case 18 and a sense/pace electrode 28 may be disposed on one of the cap 22 or circuit case 24. The electrodes 26, 28 may be configured for sensing physiological signals from tissue of patient 2. As such, electrodes 26, 28 must be electronically insulated from each other.

In one embodiment, electrode 26 may be constructed from a portion of the battery case 18. To that end, the surface of the battery case 18 and circuit case 20 may selectively be coated with an electrically insulative, biocompatible film, such as parylene, to cover the exterior surfaces except for the portion on battery case 18 that defines the electrode 26. In that embodiment, the electrode 28, therefore resides on an electrically insulated portion of the housing 16, such as the cap 22.

However, those skilled in the art will appreciate that the physiological signal generated by electrodes 26, 28 is still susceptible to noise signals resulting from the battery supply currents in the conventional battery construction, even with this electrical isolation. In using the battery case 18 as an electrode, supply currents associated with delivery of energy from the battery generate noise signals that corrupt the physiological signal.

In other words, because the conventional battery construction utilizes the battery case as a common return for the supply current path, the sensed physiological signal sensed by the electrode 26 on the battery case is corrupted by the supply current signal. In particular, in a conventional battery construction having a non-isolated case, the battery current flows through the battery case, resulting in a voltage drop. The voltage pulse is coupled to the battery case electrode and superimposed on the sensed physiological signal.

Figure 3:
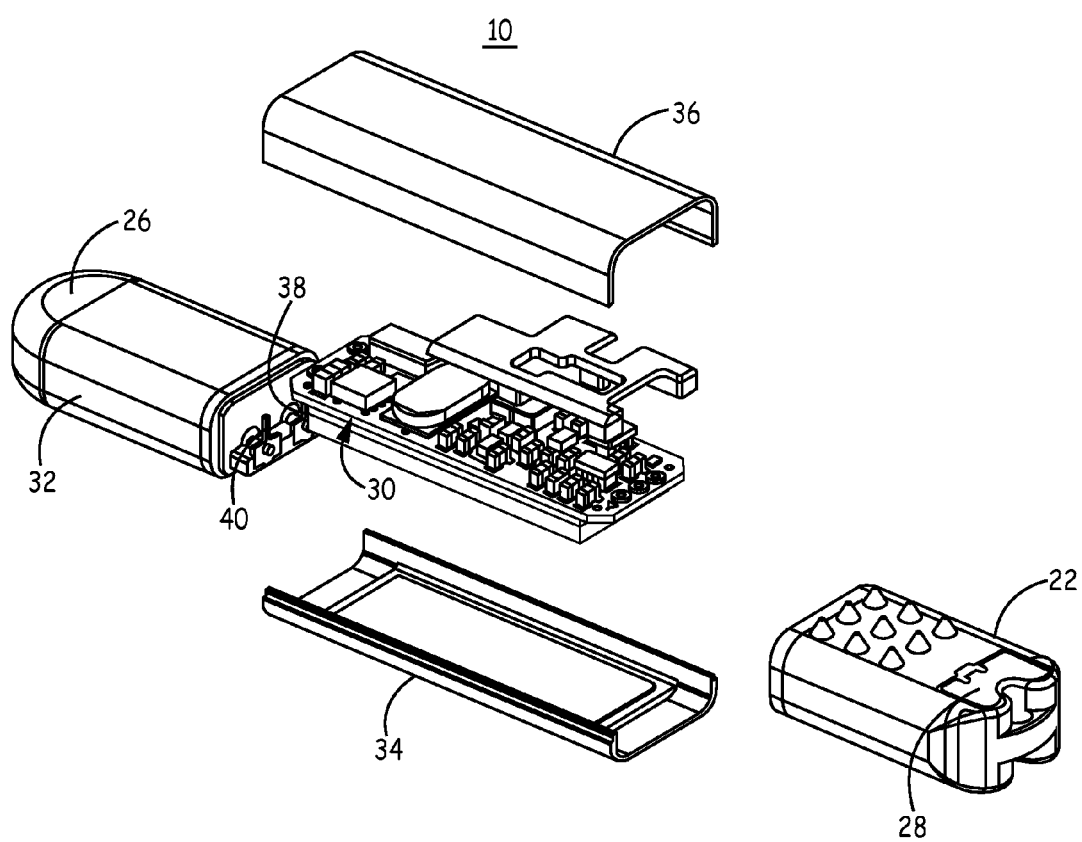
FIG. 3 depicts a perspective view of the exemplary components of the implantable medical device of FIG. 2.

FIG. 3 depicts a perspective view of the exemplary components of the IMD 10. IMD 10 includes operational circuitry 30 that is powered by an energy source such as battery 32. The battery 32 may comprise of a conventional $CF_x$, $LiCF_x$, $LiMnO_2$, or $LiI_2$ cell that includes components such as an anode, a cathode, a current collector, a separator, an insulator disk, an insulator layer, and other internal components, all of which are enclosed inside the battery case 18. It will be appreciated that the battery 32 can also contain an electrolyte (not specifically shown), such as a liquid electrolyte, for facilitating ionic transport and forming a conduction pathway between the anode and the cathode.

The operational circuitry 30 is configured to facilitate the functionality of the IMD 10. Such functionality may include sensing physiological events and/or providing electrical stimulation to the tissue of patient 2 through the electrodes 26, 28. Some exemplary electrical components that may be included in the operational circuitry 30 are illustrated in the circuit of the device(s) described in U.S. Pat. No. 5,987,352, "Minimally Invasive Implantable Device for Monitoring Physiologic Events" to Klein et al., incorporated herein by reference in its entirety. Operational circuitry 30 is disposed within shells 34, 36, which together form the circuit case 20. Shells 34, 36 are joined together and further coupled to the battery case 18 through any suitable techniques, such as welding, to form hermetically sealed housing 16.

Furthermore, the battery case 18 includes, on a closed end, a first feedthrough 38 and a second feedthrough 40 that are coupled to the battery anode and cathode. The first feedthrough 38 defines the positive terminal of the battery while the second feedthrough 40 defines the negative terminal of the battery. The battery 32 is coupled to the operational circuitry 30 through the first feedthrough 38 and the second feedthrough 40 to power the operational circuitry 30. Those of skill in the art can appreciate that under the above-described conditions, the battery case 18 will be neutral. Unlike conventional embodiments where the case is coupled to one of the negative terminal or positive terminal, the battery of the present disclosure is neither at a negative potential or a positive potential. Such a battery construction is disclosed in U.S. Pat. App. No. US2011/0247204, "Integrated Mandrel", to Viavattine et al., incorporated herein by reference in its entirety.

Components residing on the cap 22 (such as electrode 28) are coupled to the operational circuitry through a third feedthrough (not shown). The construction of first, second and third feedthroughs such as those coupling to the operational circuitry of the present disclosure is known and includes feedthroughs described in U.S. App. No. US20070150020, "Externally oriented battery feedthrough with integral connector" to Aamodt et al., incorporated herein by reference in its entirety.

The construction of the battery with feedthroughs for formation of the positive and negative terminal separates the battery case from the common return pathway of the current path between the battery 32 and the operational circuit 30. Nevertheless, the inventors of the present invention have observed that even with the electrically isolated battery case 18, an artifact/noise signal is still developed across the battery case 18 during delivery of current to the operational circuit 30.

Without intending to be bound by theory, the artifact/noise signal is associated with a voltage drop, on the order of 50 uV/1 mA, that is directly in line with the electrode 26 disposed on the battery case 18. The voltage drop is associated with leakage conduction between the battery case 18 and internal battery components, e.g., electrolyte. The inventors of the present disclosure have observed that the artifact or noise signal is generated owing to changes in battery supply current such as high current events including, telemetry data transmission, the processor being turned on/off, memory program/erase operations, or other high current operations. The artifact or noise signal resulting from the leakage conduction is coupled to the physiological signal amplifier input. Moreover, the artifact/noise signal may even be superimposed to a normal sensed physiological signal. In any event, the noise signal and/or physiological signal are amplified by the physiological signal amplifier processed by the IMD 10 processor. In the typical scenario, a physiological signal such as an ECG signal is expected to be in the range of 5 to 100 uV with a median value of 25 uV for P waves. The magnitude of the artifact/noise signal is comparable to typical P waves and the nominal threshold settings for the R wave detector.

Conventional devices are provided with a battery case for encasing the internal components of the battery and the encased battery is then enclosed in an IMD housing. Unlike the conventional devices, the battery case of the present disclosure forms the device housing without the need for an IMD housing to enclose the battery assembly. This provides a less bulky battery assembly and, consequently, can be used to facilitate miniaturization of the medical device. Moreover, the structural arrangement of the present disclosure utilizing the battery case 18 as part of the IMD 10 housing further facilitates a reduction in the number of components required for the functionality of IMD 10. For example, using the battery case 18 as an electrode eliminates the cost of a separate/discrete electrode while also eliminating the need for feedthroughs to such a discrete electrode.

Figure 4:
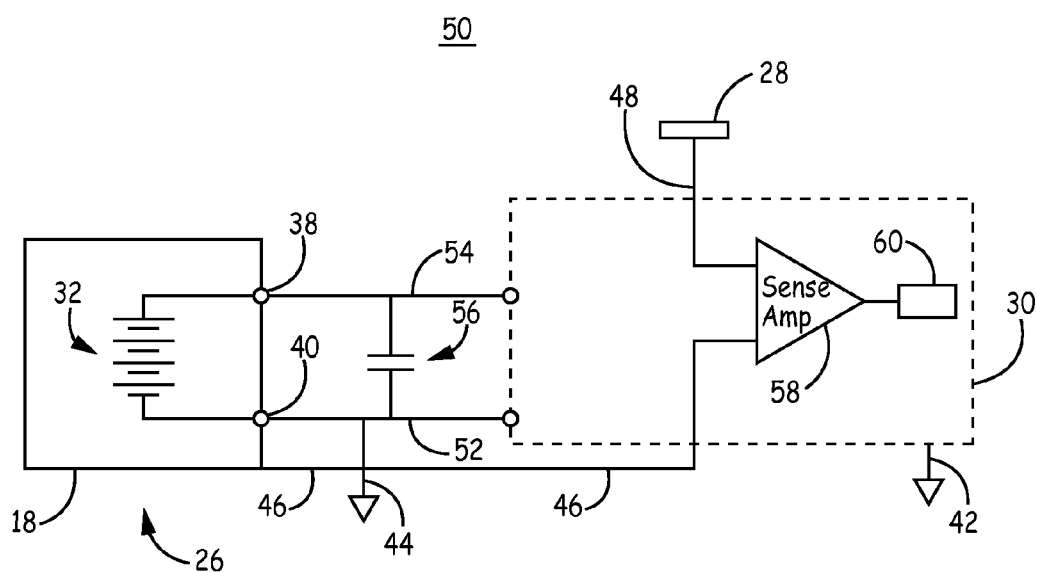
FIG. 4 depicts a schematic diagram of the implantable medical device in accordance with an exemplary embodiment.

Turning to FIG. 4, a schematic diagram of IMD 10 in accordance with an exemplary embodiment is depicted. Schematic diagram 50 is a functional schematic diagram of the circuitry associated with the sensing of physiological signals by the electrodes 26, 28. Battery 32 is enclosed within battery case 18, with a portion of the battery case 18 also functioning as electrode 26. The supply rails 52, 54 defining the current path for delivery of energy through the operational circuit 30 are coupled to the battery 32 through feedthroughs 38, 40 to achieve electrical isolation of the battery's active components from battery case 18. An optional capacitor 56 may be coupled in parallel with the supply rails 52, 54.

Electrodes 26, 28 obtain a signal from the patient 2 that is transmitted to an input mechanism 58, drawn here as a differential amplifier for simplicity only. In particular, the electrode 26 (on battery case 18) is directly coupled to the first input node of the input mechanism 58 through a conductive trace 46, while the electrode 28 is routed directly through a conductive trace 48 or through two or more conductive traces on the operational circuit 30 to couple to a second input node of the input mechanism 58.

Further, the conductive trace 46 is directly coupled to the negative terminal of the battery 32 and to the common (ground) reference 44 of the operational circuit 30. This ground connection 44 may be different from the ground reference connection 42 for the remainder of the components in operational circuit 30. The coupling of the negative terminal of the battery 32 to the conductive trace 46 may be made at the intersection of feedthrough 40 for a direct connection to the negative supply rail 52. This configuration facilitates a substantial minimization (or elimination) of supply current flowing through the sense pathway that provides an input to input mechanism 58. As such, the conductive trace 46 that couples electrode 26 to the input mechanism 58 defines a sense pathway that is electrically isolated from the primary supply current pathway through feedthrough 40. In an alternative embodiment, the resistance of the conductive trace 46 is minimized (relative to the resistance of other conductive pathways in the operational circuit) to further isolate the sense pathway from the primary supply current pathway.

The output of the input mechanism 58 is fed to processing components 60 of the operational circuit 30, such as a QRS detector and an A/D converter, for processing and detection of various cardiac anomalies. The data output from the processing components 60 may be converted, compressed, formatted and marked or reformulated if desired before the data is stored. Additionally, the data output may be transmitted to an external device, such as programmer 14, for analysis.

Figure 5:
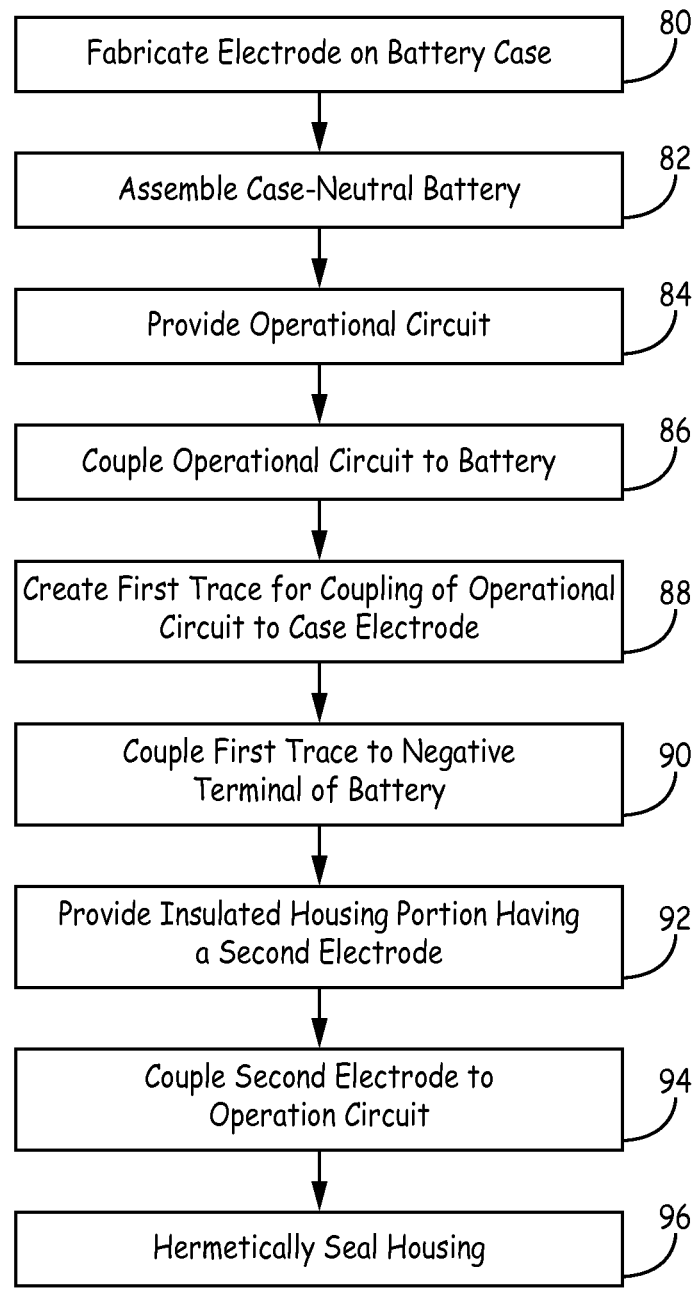
FIG. 5 is a flowchart that illustrates an example method of constructing an implantable medical device for sensing physiological signals of a patient.

FIG. 5 is a flowchart that illustrates an example method of constructing an implantable medical device for sensing physiological signals of a patient. The method is not limited to the specific tasks, or order of tasks, but rather some tasks may be combined or skipped without departing from the spirit and scope of the invention. An example of the device so constructed may include the IMD 10 that is configured for implantation in biological tissue of a patient. A device constructed in accordance with the method provides a pair of electrodes, with an appropriate electrode separation, that are disposed on a housing of the IMD 10 for sensing physiological signals from the patient.

A first of the pair of electrodes is defined on a portion of the IMD 10 housing that encases internal components of the battery (80). In one example, the battery case (first) electrode may be constructed by selectively coating a conductive battery case with an electrical insulating material, such as parylene, so as to expose only a portion of the housing that is desired to define the first electrode. In another example, the first electrode may be formed by coupling a discrete electrode onto the battery case.

The battery case is formed having a neutral case (82). In one example, the battery is constructed having feedthroughs for connecting to the conductive material of the battery. On the exterior of the battery case, the feedthroughs define the positive and negative terminals.

Further, an operational circuit is provided (84). The battery is coupled to the operational circuit through the feedthroughs to supply power to the circuit (86). The operational circuit includes various components that enable the functionality ascribed to the device. In one embodiment, the functionality includes sensing physiological signals, such as ECG signals associated with cardiac activity, of the patient. Thusly, the operational circuit may include an input mechanism such as a sense amplifier.

The input mechanism is coupled to the first electrode through a conductive pathway that is electrically isolated from the current pathway between the battery and the operational circuit (88). In other words, a third terminal is formed on the battery case, and the third terminal is directly connected to a first node of the input mechanism through, for example, a first conductive trace. Additionally, the second conductive trace directly coupling the input mechanism is coupled to the negative terminal (90). The coupling to the negative terminal is made via, for example, a second conductive trace prior to the connection of the negative terminal to the operational circuit.

A second of the pair of electrodes is disposed on an electrically insulated portion of the IMD 10 housing (92). The second electrode is coupled to a second node the input mechanism (94).

A circuit case is provided for enclosing the operational circuit. The electrically insulated portion of the IMD 10 may be a separate and/or discrete component or an integral component of the circuit case. The battery case, the circuit case and optionally the insulated portion are coupled in an end-to-end configuration to form a hermetically sealed housing of IMD 10 (96).

The coupling of the first and second electrodes to the input mechanism defines a physiological signal pathway that is electrically isolated from the current pathway. A device constructed in accordance with the foregoing enables detection of a physiological signal without artifacts/noise signals attributed to the battery power supply.

As can be appreciated, devices in accordance with the present disclosure facilitate a method of sensing a physiological signal from biological tissue of a patient. The method includes disposing the implantable medical device within the biological tissue for sensing physiological signals of the patient. The implantable medical device includes an energy source, such as a battery, having a battery case enclosing internal components of the battery and a first electrode coupled to an external surface of the battery case. The implantable medical device further includes a circuit case that encloses an operational circuit including control components for controlling the operation of the implantable medical device. A second electrode is disposed on the outer surface of one of the circuit case or the battery case.

Furthermore, the method of sensing physiological signals includes exposing the outer surfaces of the battery case and the circuit case to the biological tissue. Also, the method includes providing power from the internal component of the battery to the operational circuit for sensing physiological signals and transmitting the sensed signals between the biological tissue and the first and second electrodes.

Accordingly, the techniques of the present disclosure facilitate miniaturization of devices, such as IMD 10, that are configured for implantation in a patient. The techniques facilitate construction of devices having a form factor and size that may sense physiological signals and/or provide therapy with a minimal number of components relative to those that would be required utilizing conventional techniques. Among other things, the techniques described in this disclosure facilitate electrode arrangements having an appropriate spatial separation for sensing of the physiological signals and providing the stimulation therapy.

The memory devices of the present disclosure may include non-transitory computer readable storage media storing instructions that, when executed by one or more processing circuits, cause the modules to perform various functions attributed to IMD 10. The storage media may include any computer-readable storage media with the sole exception being a transitory, propagating signal.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. It should also be understood that various changes can be made in the function and arrangement of elements without departing from the scope of the disclosure as set forth in the appended claims and the legal equivalents thereof.

What is claimed is:

1. An implantable medical device, comprising:
    a hermetically sealed housing having first and second portions;
    a battery disposed within housing, wherein an enclosure of the battery is defined by the first portion of the housing;
    an operational circuit disposed within the second portion of the housing;
    a feedthrough assembly disposed on the first portion configured for electrical coupling of a positive terminal and a negative terminal of the battery to the operational circuit to define a current pathway;
    a first electrode disposed on the housing and electrically coupled to the operational circuit; and
    a second electrode disposed on an outer surface of the first portion and electrically coupled to the operational circuit through a first conductive trace, wherein the first conductive trace is decoupled from the current pathway.

2. The implantable medical device of claim 1, wherein the coupling between the first electrode and the second electrode to the operational circuit defines a physiological signal pathway that is electrically isolated from the current pathway.

3. The implantable medical device of claim 1, further comprising a second conductive trace coupling the negative terminal to the first conductive trace.

4. The implantable medical device of claim 3, further comprising a third conductive trace coupling the first conductive trace to a ground terminal in common with the operational circuit.

5. The implantable medical device of claim 1, wherein at least one of the first electrode and the second electrode are directly coupled to an input mechanism disposed within the operational circuit.

6. The implantable medical device of claim 5, wherein the input mechanism comprises circuitry configured to receive an analog signal representation of a sensed physiological signal.

7. The implantable medical device of claim 6, wherein the input mechanism is a differential amplifier having a first terminal coupled to the first electrode and a second terminal coupled to the second electrode.

8. The implantable medical device of claim 1, wherein the feedthrough assembly includes an electrically insulative component to electrically isolate the positive and negative terminals from the housing.

9. The implantable medical device of claim 1, wherein the first electrode is disposed on an electrically insulated section of the second portion.

10. The implantable medical device of claim 1, further comprising an insulator selectively coupled to the housing wherein the second electrode is defined by a portion of the housing that is not covered by the insulator.

11. The implantable medical device of claim 10, wherein the first electrode is disposed on the insulator.

12. The implantable medical device of claim 1, wherein the first and second electrodes are configured for sensing cardiac signals.

13. The implantable medical device of claim 1, wherein the first and second electrodes are configured for delivery of an electrical stimulation therapy generated by the battery.

14. The implantable medical device of claim 1, wherein the first portion of the housing includes a first interior chamber and the second portion includes a second interior chamber, and wherein the first interior chamber is arranged in an end to end configuration with the second interior chamber.

15. The implantable medical device of claim 14, wherein the feedthrough assembly electrically isolates the first interior chamber from the second interior chamber, the feedthrough assembly including first and second terminal pins extending therethrough for electrical coupling of the battery to the operational circuit.

16. The implantable medical device of claim 1, wherein the feedthrough assembly is disposed on the first portion of the housing and is electrically isolated from the first portion of the housing.

* * * * *